US008774914B2

(12) United States Patent
Wagner

(10) Patent No.: US 8,774,914 B2
(45) **Date of Patent: *Jul. 8, 2014**

(54) SYSTEMS AND METHODS FOR STIMULATING CELLULAR FUNCTION IN TISSUE

(71) Applicant: Highland Instruments, Somerville, MA (US)

(72) Inventor: Timothy A. Wagner, Somerville, MA (US)

(73) Assignee: Highland Instruments, Inc., Somerville, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,613

(22) Filed: Nov. 1, 2013

(65) Prior Publication Data

US 2014/0058295 A1 Feb. 27, 2014

Related U.S. Application Data

(63) Continuation of application No. 13/216,313, filed on Aug. 24, 2011, now Pat. No. 8,594,783.

(51) Int. Cl.

| | |
|---|---|
| ***A61N 1/36*** | (2006.01) |
| ***A61N 1/32*** | (2006.01) |
| ***A61N 1/20*** | (2006.01) |
| *A61N 7/00* | (2006.01) |
| *A61F 7/00* | (2006.01) |
| *A61B 18/00* | (2006.01) |

(52) U.S. Cl.

CPC *A61N 1/36* (2013.01); *A61N 1/325* (2013.01); *A61N 1/326* (2013.01); *A61N 1/327* (2013.01); *A61N 2007/0026* (2013.01); *A61N 1/36025* (2013.01); *A61N 1/205* (2013.01); *A61F 7/00* (2013.01); *A61B 2018/00994* (2013.01); *A61N 7/00* (2013.01); *A61N 1/36021* (2013.01)

USPC .......................................................... 607/3

(58) Field of Classification Search

CPC ................................................ A61N 1/36071

USPC ....................................... 607/3, 45–46, 152

See application file for complete search history.

(56) References Cited

U.S. PATENT DOCUMENTS 8,594,783 B2 * 11/2013 Wagner .............................. 607/3

* cited by examiner

*Primary Examiner* — Amanda Patton

(74) *Attorney, Agent, or Firm* — Mark S. Leonardo; Adam M. Schoen; Brown Rudnick LLP

(57) ABSTRACT

The invention generally relates to systems and methods for stimulating cellular function in biological tissue. In certain embodiments, the invention provides a method for stimulating cellular function within tissue that involves providing a first type of energy to a region of tissue, in which the first type is provided in an amount that inhibits cellular function within the region of tissue, and providing a second type of energy to the region of tissue, in which the second type is provided in an amount that facilitates cellular function within the region of tissue, wherein the combined effect stimulates cellular function within the tissue.

17 Claims, 6 Drawing Sheets

SYSTEMS AND METHODS FOR STIMULATING CELLULAR FUNCTION IN TISSUE

RELATED APPLICATION

This patent application is a continuation of U.S. nonprovisional patent application Ser. No. 13/216,313, filed Aug. 24, 2011, the content of which is incorporated by reference herein in its entirety.

GOVERNMENT SUPPORT

This invention was made with Government support under Grant Number R43NS062530 awarded by the National Institute of Neurological Disorders and Stroke (NINDS) of the National Institute of Health (NIH) and Contract No. W31P4Q-09-C-0117 awarded by Defense Advanced Research Projects Agency (DARPA). The Government has certain rights in this invention.

FIELD OF THE INVENTION

The invention generally relates to systems and methods for stimulating cellular function in biological tissue.

BACKGROUND

Stimulation of tissue in humans and other animals is used in a number of clinical applications as well as in clinical and general biological research. In particular, stimulation of neural tissue has been used in the treatment of various diseases including Parkinson's disease, depression, and intractable pain. The stimulation may be applied invasively, e.g., by performing surgery to remove a portion of the skull and implanting electrodes in a specific location within brain tissue, or non-invasively, .e.g., transcranial direct current stimulation and transcranial magnetic stimulation.

SUMMARY

The invention recognizes that a synergistic stimulation effect in a region of tissue may be achieved by combining a first type of energy that is provided in an amount that inhibits cellular function with a second type of energy that is provided in an amount that facilitates cellular function. Data herein show that the stimulatory effect is greater than the summed effect of the first and second amounts of energy provided to the region of tissue.

Accordingly, methods of the invention involve providing a first type of energy to a region of tissue, in which the first type is provided in an amount that inhibits cellular function within the region of tissue, and providing a second type of energy to the region of tissue, in which the second type is provided in an amount that facilitates cellular function within the region of tissue, wherein the combined effect stimulates cellular function within the tissue. In certain embodiments, the stimulatory effect is facilitatory to the cellular function within the tissue. In other embodiments, the stimulatory effect is inhibitory to the cellular function within the tissue. The first and second types of energy may be provided simultaneously or sequentially.

Any energy sources known in the art may be used with systems of the invention. In certain embodiments, the first energy source is an electric source that produces an electric field. The electric filed may be pulsed, time varying, pulsed a plurality of time with each pulse being for a different length of time, or time invariant. In certain embodiments, the second energy source is a source that produces a mechanical field, such as an ultrasound device. The mechanical filed may be pulsed, time varying, or pulsed a plurality of time with each pulse being for a different length of time. In certain embodiments, the electric field and/or the mechanical field is focused. The other permutations are also attainable, where the effect direction (i.e., inhibitory or facilitatory) is dependent on the electrical and/or ultrasound source transducer parameters and/or the electrical and/or ultrasound field parameters.

The first and second energy sources may be applied to any tissue. In certain embodiments, the first and second energy sources are applied to a structure or multiple structures within the brain or the nervous system such as the dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, and spinal cord. In particular embodiments, the tissue is neural tissue, and the affect of the stimulation alters neural function past the duration of stimulation.

Another aspect of the invention provides a system for stimulating cellular function within tissue that includes an ultrasound device configured to emit a mechanical field that inhibits cellular function within the region of tissue, and an electric source configured to emit an electric field that facilitates cellular function within the region of tissue, the system being configured such that the ultrasound device and the electric source target the same region of tissue and the combined effect stimulates cellular function in a facilitatory manner within the region of tissue. Similarly, the ultrasound source could be provided in a facilitatory manner and the electrical source in an inhibitory manner such that the overall effect on cellular function is inhibitory. The other permutations are also attainable, where the effect direction (i.e., inhibitory or facilitatory) is dependent on the electrical and/or ultrasound source transducer parameters and/or the electrical and/or ultrasound field parameters.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein.

DETAILED DESCRIPTION

Figure 1:
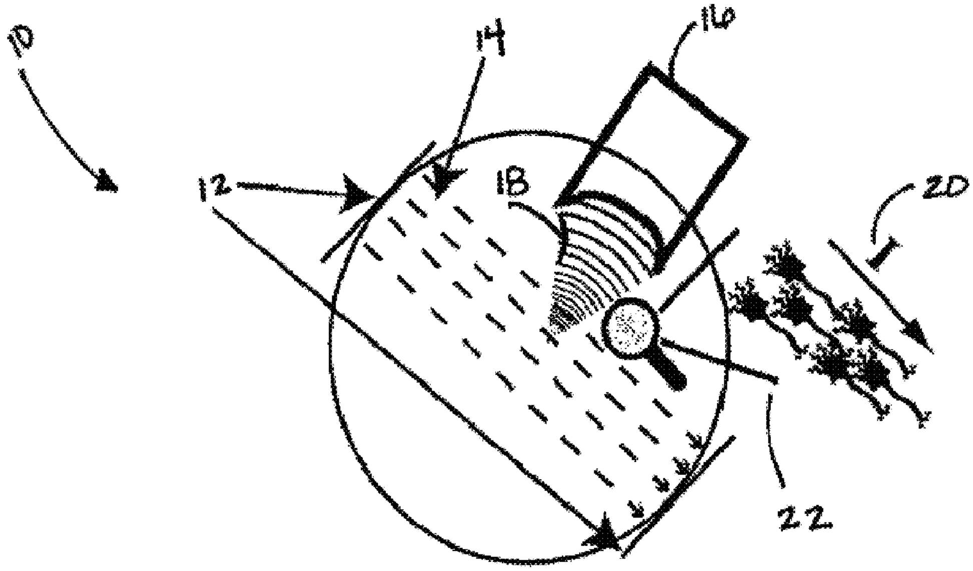
FIG. 1 is a plan view of one embodiment of an apparatus for stimulating biological tissue constructed in accordance with the principles of the present disclosure.

It is envisioned that the present disclosure may be used to stimulate biological tissue in-vivo comprising an electric source that is placed on and/or in the body to generate an electric field and a means for altering the permittivity of tissue relative to the electric field, whereby the alteration of the tissue permittivity relative to the electric field generates a displacement current in the tissue. The exemplary embodiments of the apparatuses and methods disclosed can be employed in the area of neural stimulation, where amplified, focused, direction altered, and/or attenuated currents could be used to alter neural activity via directly stimulating neurons, depolarizing neurons, hyperpolarizing neurons, modifying neural membrane potentials, altering the level of neural cell excitability, and/or altering the likelihood of a neural cell firing. Likewise, the method for stimulating biological tissue may also be employed in the area of muscular stimulation, including cardiac stimulation, where amplified, focused, direction altered, and/or attenuated currents could be used to alter muscular activity via direct stimulation, depolarizing muscle cells, hyperpolarizing muscle cells, modifying membrane potentials, altering the level of muscle cell excitability, and/or altering the likelihood of cell firing. Similarly, it is envisioned that the present disclosure may be employed in the area of cellular metabolism, physical therapy, drug delivery, and gene therapy. Furthermore, stimulation methods described herein can result in or influence tissue growth (such as promoting bone growth, directing neural growth or regeneration, and/or interfering with a tumor).

Detailed embodiments of the present disclosure are disclosed herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

The components of the tissue stimulation method according to the present disclosure are fabricated from materials suitable for a variety medical applications, such as, for example, polymerics, gels, films, and/or metals, depending on the particular application and/or preference. Semi-rigid and rigid polymerics are contemplated for fabrication, as well as resilient materials, such as molded medical grade polyurethane, as well as flexible or malleable materials. The motors, gearing, electronics, power components, electrodes, and transducers of the method may be fabricated from those suitable for a variety of medical applications. The method according to the present disclosure may also include circuit boards, circuitry, processor components, etc. for computerized control. One skilled in the art, however, will realize that other materials and fabrication methods suitable for assembly and manufacture, in accordance with the present disclosure, also would be appropriate.

The following discussion includes a description of the components and exemplary methods for generating currents in biological tissues in accordance with the principles of the present disclosure. Alternate embodiments are also disclosed. Reference will now be made in detail to the exemplary embodiments of the present disclosure illustrated in the accompanying figures wherein like reference numerals indicate the similar parts throughout the figures.

Turning now to FIG. 1, which illustrates an exemplary embodiment of an apparatus 10 to alter currents, e.g., amplify, focus, alter direction, and/or attenuate in the presence of an applied electric field or applied current source by the combined application of a mechanical field within a biological material to stimulate the biological cells and/or tissue in accordance with the present disclosure. For example, the apparatus 10 illustrated in FIG. 1 according to the present disclosure may be applied to the area of neural stimulation. An initial source electric field 14 results in a current in the tissue. The electric field 14 is created by an electric source, current or voltage source. As described in further detail below, the permittivity of the tissue is altered relative to the electric field, for example by a mechanical field, thereby generating an additional displacement current.

Electrodes 12 are applied to the scalp and generate a low magnitude electric field 14 over a large brain region. While electrodes 12 are used and applied to the scalp in this exemplary embodiment, it is envisioned that the electrodes may be applied to a number of different areas on the body including areas around the scalp. It is also envisioned that one electrode may be placed proximal to the tissue being stimulated and the other distant, such as one electrode on the scalp and one on the thorax. It is further envisioned that electric source could be mono-polar with just a single electrode, or multi-polar with multiple electrodes. Similarly, the electric source may be applied to tissue via any medically acceptable medium. It is also envisioned that means could be used where the electric source does not need to be in direct contact with the tissue, such as for example, inductive magnetic sources where the entire tissue region is placed within a large solenoid generating magnetic fields or near a coil generating magnetic fields, where the magnetic fields induce electric currents in the tissue.

The electric source may be direct current (DC) or alternating current (AC) and may be applied inside or outside the tissue of interest. Additionally, the source may be time varying. Similarly, the source may be pulsed and may be comprised of time varying pulse forms. The source may be an impulse. Also, the source according to the present disclosure may be intermittent.

A mechanical source such as an ultrasound source 16 is applied on the scalp and provides concentrated acoustic energy 18, i.e., mechanical field to a focused region of neural tissue, affecting a smaller number of neurons 22 than affected by the electric field 14, by the mechanical field 18 altering the tissue permittivity relative to the applied electric field 14, and thereby generating the altered current 20. The mechanical source may be any acoustic source such as an ultrasound device. Generally, such device may be a device composed of electromechanical transducers capable of converting an electrical signal to mechanical energy such as those containing piezoelectric materials, a device composed of electromechanical transducers capable of converting an electrical signal to mechanical energy such as those in an acoustic speaker that implement electromagnets, a device in which the mechanical source is coupled to a separate mechanical apparatus that drives the system, or any similar device capable of converting chemical, plasma, electrical, nuclear, or thermal energy to mechanical energy and generating a mechanical field.

Furthermore, the mechanical field could be generated via an ultrasound transducer that could be used for imaging tissue. The mechanical field may be coupled to tissue via a bridging medium, such as a container of saline to assist in the focusing or through gels and/or pastes which alter the acoustic impedance between the mechanical source and the tissue. The mechanical field may be time varying, pulsed, an impulse, or may be comprised of time varying pulse forms. It is envisioned that the mechanical source may be applied inside or outside of the tissue of interest. There are no limitations as to the frequencies that can be applied via the mechanical source, however, exemplary mechanical field frequencies range from the sub kHZ to 1000 s of MHz. Additionally, multiple transducers providing multiple mechanical fields with similar or differing frequencies, and/or similar or different mechanical field waveforms may be used—such as in an array of sources like those used in focused ultrasound arrays. Similarly, multiple varied electric fields could also be applied. The combined fields, electric and mechanical, may be controlled intermittently to cause specific patterns of spiking activity or alterations in neural excitability. For example, the device may produce a periodic signal at a fixed frequency, or high frequency signals at a pulsed frequency to cause stimulation at pulse frequencies shown to be effective in treating numerous pathologies. Such stimulation waveforms may be those implemented in rapid or theta burst TMS treatments, deep brain stimulation treatments, epidural brain stimulation treatments, spinal cord stimulation treatments, or for peripheral electrical stimulation nerve treatments. The ultrasound source may be placed at any location relative to the electrode locations, i.e., within, on top of, below, or outside the same location as the electrodes as long as components of the electric field and mechanical field are in the same region. The locations of the sources should be relative to each other such that the fields intersect relative to the tissue and cells to be stimulated, or to direct the current alteration relative to the cellular components being stimulated.

The apparatus and method according to the present disclosure generates capacitive currents via permittivity alterations, which can be significant in magnitude, especially in the presence of low frequency applied electric fields. Tissue permittivities in biological tissues are much higher than most other non biological materials, especially for low frequency applied electric fields where the penetration depths of electric fields are highest. This is because the permittivity is inversely related to the frequency of the applied electric field, such that the tissue permittivity magnitude is higher with lower frequencies. For example, for electric field frequencies below 100,000 Hz, brain tissue has permittivity magnitudes as high as or greater than 10^8 (100,000,000) times the permittivity of free space (8.854*10^-12 farad per meter), and as such, minimal local perturbations of the relative magnitude can lead to significant displacement current generation. As the frequency of the electric field increases, the relative permittivity decreases by orders of magnitude, dropping to magnitudes of approximately 10^3 times the permittivity of free space (8.854*10^-12 farad per meter) for electric field frequencies of approximately 100,000 Hz. Additionally, by not being constrained to higher electric field frequencies, the method according to the present disclosure is an advantageous method for stimulating biological tissue due to lowered penetration depth limitations and thus lowered field strength requirements. Additionally, because displacement currents are generated in the area of the permittivity change, focusing can be accomplished via the ultrasound alone. For example, to generate capacitive currents via a permittivity perturbation relative to an applied electric field as described above, broad DC or a low frequency electric source field well below the cellular stimulation threshold is applied to a brain region but stimulation effects are locally focused in a smaller region by altering the tissue permittivity in the focused region of a mechanical field generated by a mechanical source such as an ultrasound source. This could be done noninvasively with the electrodes and the ultrasound device both placed on the scalp surface such that the fields penetrate the tissue surrounding the brain region and intersect in the targeted brain location, or with one or both of the electrodes and/or the ultrasound device implanted below the scalp surface (in the brain or any of the surrounding tissue) such that the fields intersect in the targeted region.

A displacement current is generated by the modification of the permittivity in the presence of the sub threshold electric field and provides a stimulatory signal. In addition to the main permittivity change that occurs in the tissues, which is responsible for stimulation (i.e., the generation of the altered currents for stimulation), a conductivity change could also occur in the tissue, which secondarily alters the ohmic component of the currents. In a further embodiment, the displacement current generation and altered ohmic current components may combine for stimulation. Generally, tissue conductivities vary slightly as a function of the applied electric field frequency over the DC to 100,000 Hz frequency range, but not to the same degree as the permittivities, and increase with the increasing frequency of the applied electric field. Additionally in biological tissues, unlike other materials, the conductivity and permittivity do not show a simple one-to-one relationship as a function of the applied electric field frequency. The permittivity ranges are as discussed above.

Although the process described may be accomplished at any frequency of the applied electric field, the method in an exemplary embodiment is applied with lower frequency applied electric fields due to the fact the permittivity magnitudes of tissues, as high as or greater than 10^8 times the permittivity of free space, and the electric field penetration depths are highest for low frequency applied electric fields. Higher frequency applied electric fields may be less desirable as they will require greater radiation power to penetrate the tissue and/or a more pronounced mechanical source for permittivity alteration to achieve the same relative tissue permittivity change, i.e., at higher applied electric field frequencies the permittivity of the tissue is lower and as such would need a greater overall perturbation to have the same overall change in permittivity of a tissue as at a lower frequency. Applied electric field frequencies in the range of DC to approximately 100,000 Hz frequencies are advantageous due to the high tissue permittivity in this frequency band and the high penetration depth for biological tissues at these frequencies. In this band, tissues are within the so called 'alpha dispersion band' where relative tissue permittivity magnitudes are maximally elevated (i.e., as high as or greater than 10^8 times the permittivity of free space). Frequencies above approximately 100,000 to 1,000,000 Hz for the applied electric fields are still applicable for the method described in generating displacement currents for the stimulation of biologic cells and tissue, however, both the tissue permittivity and penetration depth are limited for biological tissues in this band compared to the previous band but displacement currents of sufficient magnitude can still be generated for some applications. In this range, the magnitude of the applied electric field will likely need to be increased, or the method used to alter the permittivity relative to the applied electric field increased to bring about a greater permittivity change, relative to the tissue's permittivity magnitude for the applied electric field frequency. Additionally, due to potential safety concerns for some applications, it may be necessary to limit the time of application of the fields or to pulse the fields, as opposed to the continuous application that is possible in the prior band. For tissues or applications where the safety concerns preclude the technique in deeper tissues, the technique could still be applied in more superficial applications in a noninvasive manner or via an invasive method. Higher frequency applied electric fields, above 1,000,000 to 100,000,000 Hz, could be used in generating displacement currents for the stimulation of biologic cells and tissue. However, this would require a more sufficient permittivity alteration or electromagnetic radiation, and as such is less than ideal in terms of safety than the earlier bands. For frequencies of the applied electric field above 100,000,000 Hz, biologic cell and tissue stimulation may still be possible, but may be limited for specialized applications that require less significant displacement currents.

The focus of the electric and mechanical fields to generate an altered current according to the present disclosure may be directed to various structures within the brain or nervous system including but not limited to dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, spinal cord, nerve roots, sensory organs, and peripheral nerves.

The focused tissue may be selected such that a wide variety of pathologies may be treated. Such pathologies that may be treated include but are not limited to Multiple Sclerosis, Amyotrophic Lateral Sclerosis, Alzheimer's Disease, Dystonia, Tics, Spinal Cord Injury, Traumatic Brain Injury, Drug Craving, Food Craving, Alcohol Craving, Nicotine Craving, Stuttering, Tinnitus, Spasticity, Parkinson's Disease, Parkinsonianism, Obsessions, Depression, Schizophrenia, Bipolar Disorder, Acute Mania, Catonia, Post-Traumatic Stress Disorder, Autism, Chronic Pain Syndrome, Phantom Limb Pain, Epilepsy, Stroke, Auditory Hallucinations, Movement Disorders, Neurodegenerative Disorders, Pain Disorders, Metabolic Disorders, Addictive Disorders, Psychiatric Disorders, Traumatic Nerve Injury, and Sensory Disorders. Furthermore, electric and mechanical fields to generate an altered current may be focused on specific brain or neural structures to enact procedures including sensory augmentation, sensory alteration, anesthesia induction and maintenance, brain mapping, epileptic mapping, neural atrophy reduction, neuroprosthetic interaction or control with nervous system, stroke and traumatic injury neurorehabilitation, bladder control, assisting breathing, cardiac pacing, muscle stimulation, and treatment of pain syndromes, such as those caused by migraine, neuropathies, and low-back pain; or internal visceral diseases, such as chronic pancreatitis or cancer. The methods herein could be expanded to any form of arthritis, impingement disorders, overuse injuries, entrapment disorders, and/or any muscle, skeletal, or connective tissue disorder which leads to chronic pain, central sensitization of the pain signals, and/or an inflammatory response.

In the focused region of tissue to which the mechanical fields and electrical fields are delivered, the excitability of individual neurons can be heightened to the point that the neurons can be stimulated by the combined fields, or be affected such as to cause or amplify the alteration of the neural excitability caused by the altered currents, either through an increase or decrease in the excitability of the neurons. This alteration of neural excitability can last past the duration of stimulation and thus be used as a basis to provide lasting treatment. Additionally, the combined fields can be provided in multiple, but separate sessions to have a summed, or carry-over effect, on the excitability of the cells and tissue. The combined fields can be provided prior to another form of stimulation, to prime the tissue making it more or less susceptible to alternate, follow-up forms of stimulation. Furthermore, the combined fields can be provided after an alternate form of stimulation, where the alternate form of stimulation is used to prime the tissue to make it more or less susceptible to the form of stimulation disclosed herein. Furthermore, the combined fields could be applied for a chronic period of time.

Figure 2:
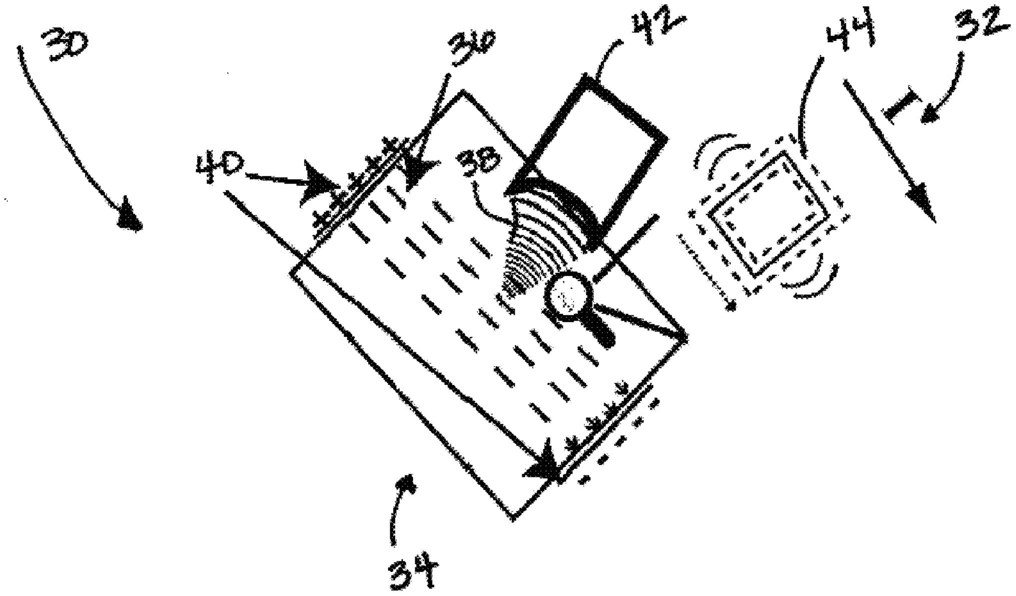
FIG. 2 is a top plan view of an exemplary embodiment of an apparatus for stimulating biological tissue constructed in accordance with the principles of the present disclosure.

FIG. 2 illustrates a set up 30 to perform a method for generating an altered current with a newly generated displacement current 32 for stimulation in biologic tissue 34 through the combined effects of an electric field 36 and a mechanical field 38. A tissue or composite of tissues 34 is placed adjacent to the anode and cathode of an electric source 40 which generates an electric field 36. The electric field 36 is combined with a mechanical, e.g., ultrasound field 38 which can be focused on the tissue 34 and generated via an ultrasound transducer 42. In a sub-region of tissue 44 where the mechanical field 38 is focused and intersects with the electric field 36, a displacement current 32 is generated. By vibrating and/or mechanically perturbing the sub-region of tissue 44, the permittivity of the tissue 44 can be altered relative to the applied electric field 36 to generate a displacement current 32 in addition to the current that would be present due to the source electric field 36 and altered due to conductivity changes in the tissue caused by the mechanical perturbation.

By providing the mechanical field 38 to the sub region of tissue 44, the permittivity can be altered within the electric field 36 by either new elements of the sub region of tissue 44 vibrating in and out of the electric field such that the continuum permittivity of the tissue is changed relative to the electric field 36, or that the bulk properties of the sub region of tissue 44 and the permittivity, or tissue capacitance, change due to the mechanical perturbation. An example of altering the permittivity within the electric field can occur when a cell membrane and extra-cellular fluid, both of different permittivities, are altered in position relative to the electric field by the mechanical field. This movement of tissues of different permittivity relative to the electric field will generate a new displacement current. The tissues could have permittivity values as high as or greater than 10^8 times the permittivity of free space, differ by orders of magnitude, and/or have anisotropic properties such that the tissue itself demonstrates a different permittivity magnitude depending on the relative direction of the applied electric field. An example of altering permittivity of the bulk tissue occurs where the relative permittivity constant of the bulk tissue is directly altered by mechanical perturbation in the presence of an electric field. The mechanical source, i.e., ultrasound source may be placed at any location relative to the electrode locations, i.e., within or outside the same location as the electrodes, as long as components of the electric field and mechanical field are in the same region.

Tissue permittivities can be altered relative to the applied electric fields via a number of methods. Mechanical techniques can be used to either alter the bulk tissue permittivity relative to an applied electric field or move tissue components of differing permittivities relative to an applied electric field. There are no specific limitations to the frequency of the mechanical field that is applied as previously discussed, however, exemplary frequencies range from the sub kHZ to 1000 s of MHz. A second electromagnetic field could be applied to the tissue, at a different frequency than the initial frequency of the applied electromagnetic field, such that it alters the tissue permittivity at the frequency dependent point of the initially applied electric field. An optical signal could also be focused on the tissues to alter the permittivity of the tissue relative to an applied electric field. A chemical agent or thermal field could also be applied to the tissues to alter the permittivity of the tissue relative to an applied electric field. These methods could also be used in combination to alter the tissue permittivity relative to an applied electric field via invasive or non-invasive methods.

Figure 3:
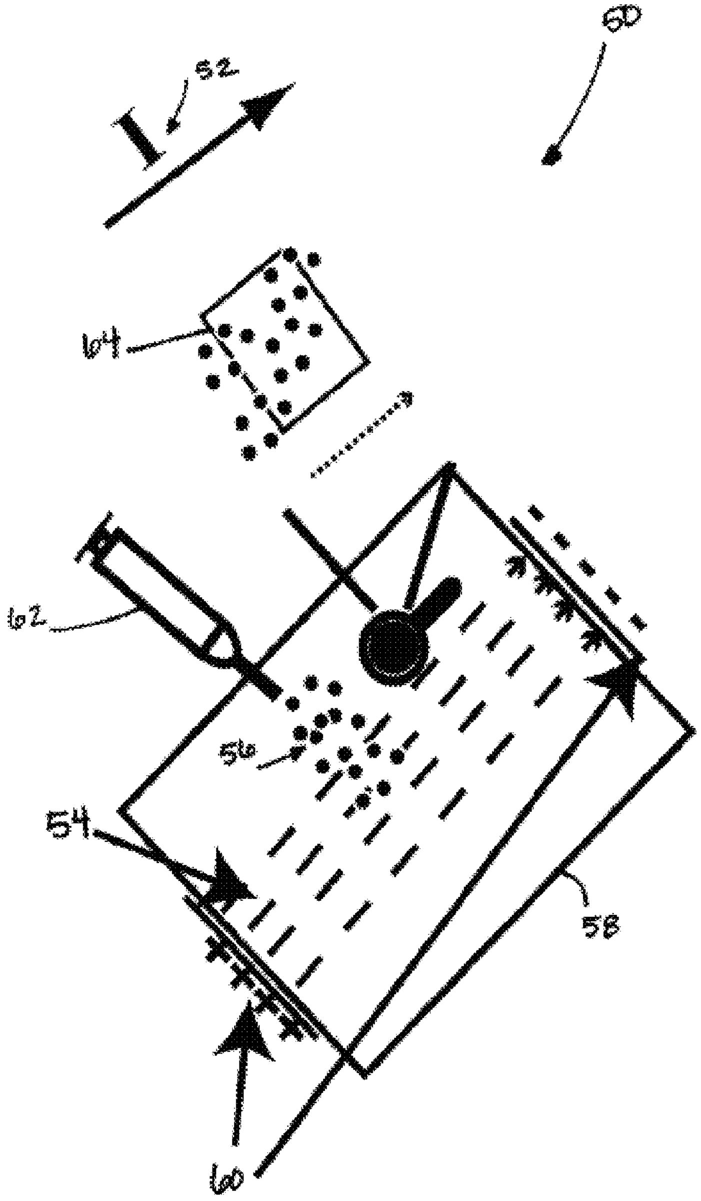
FIG. 3 is a top plan view of an exemplary embodiment of an apparatus for stimulating biological tissue implementing a chemical source for altering permittivity constructed in accordance with the principles of the present disclosure.

For example, FIG. 3 shows a set up 50 for generating an altered current with a newly generated displacement current 52 through the combined effects of an electric field 54 and a chemical agent 56. A tissue or composite of tissues 58 is placed within an electric source 60 which generates an electric field 54 and combined with chemical source 62 which releases a chemical agent 56 that can be focused on the tissue 58. In the area that the chemical agent 56 is released in the tissue 64, the electric field 54 transects the sub region of tissue 64, and the chemical agent 56 reacts with the sub region of tissue 64 to alter the tissue's relative permittivity relative to the applied electric field 54. This generates a displacement current 52 in addition to the current that would be present due to the source electric field 54. The chemical agent 56 may be any agent which can react with the tissue or cellular components of the tissue 64 to alter its permittivity relative to the electric field 54. This may be by a thermoreactive process to raise or lower the tissue 64 temperature or through a chemical reaction which alters the distribution of ions in the cellular and extra-cellular media, for instance, along ionic double layers at cell walls in the tissue 64. Similarly, the conformation of proteins and other charged components within the tissue 64 could be altered such that the permittivity of the tissue is altered relative to the low frequency electric field 54. The agent could also be any agent that adapts the permanent dipole moments of any molecules or compounds in the tissue 64, temporarily or permanently relative to the low frequency electric field 54. The chemical reaction driven by the chemical agent 56 must work rapidly enough such that the permittivity of the tissue is quickly altered in the presence of the electric field 54 in order to generate the displacement current 52. The reaction may also be such as to fluctuate the permittivity, such that as the permittivity continues to change displacement currents continue to be generated. In addition to the main permittivity change that occurs in the tissues, a conductivity change could also occur in the tissue, which secondarily alters the ohmic component of the currents. A biological agent may be used in place of, or in addition to, the chemical agent 56. This embodiment may have particular application for focused drug delivery where an additional chemical or biological agent is included to assist in therapy of the tissue, or where the altered current could drive an additional electrochemical reaction for therapy. For example, this could be used in areas such as focused gene therapy or focused chemotherapy.

Figure 4:
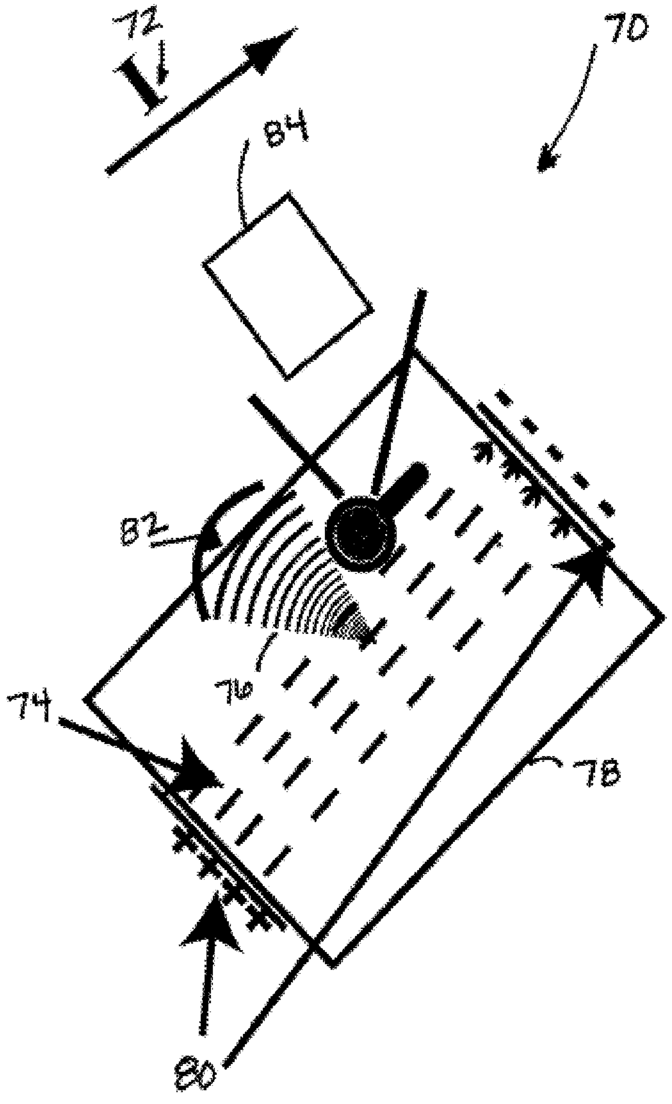
FIG. 4 is a top plan view of an exemplary embodiment of an apparatus for stimulating biological tissue implementing a radiation source for altering permittivity constructed in accordance with the principles of the present disclosure.

Another example is shown in FIG. 4, which illustrates a set up 70 for applying a method for generating an altered current with a newly generated displacement current 72 through the combined effects of a low frequency electric field 74 and an electromagnetic radiation field 76. A tissue or composite of tissues 78 is placed within a low frequency electric field 74 which is generated by an electric source 80 and combined with radiation source 82 which generates a radiation field 76 that can be focused on the tissue 78. In the area that the radiation field 76 is focused in the tissue 78, the electric field 74 transects the sub component of tissue 84, where the radiation field 76 interacts with the sub component of tissue 84 to alter the tissue's relative permittivity relative to the applied electric field 74, and as such generates a displacement current 72 in addition to the current that would be present due to the source electric field 74 or the radiation source field 76 alone. The electromagnetic radiation field 76 could, for example, interact with the tissue 84 by altering its temperature through ohmic processes, alter the distribution of ions in the cellular and extra-cellular media for instance along ionic double layers along cell walls through the electric forces acting on the ions, or alter the conformation of proteins and other charged components within the tissue through the electric forces such that the permittivity of the tissue is altered relative to the low frequency electric field 74. Furthermore, the electromagnetic field 76, could interact with the tissue 84 by moving components of the tissue via electrorestrictive forces, as would be seen in anisotropic tissues, to alter the continuum permittivity of the tissue relative to the low frequency electric field 74. In addition to the main permittivity change that occurs in the tissues, a conductivity change could also occur in the tissue, which secondarily alters the ohmic component of the currents.

Figure 5:
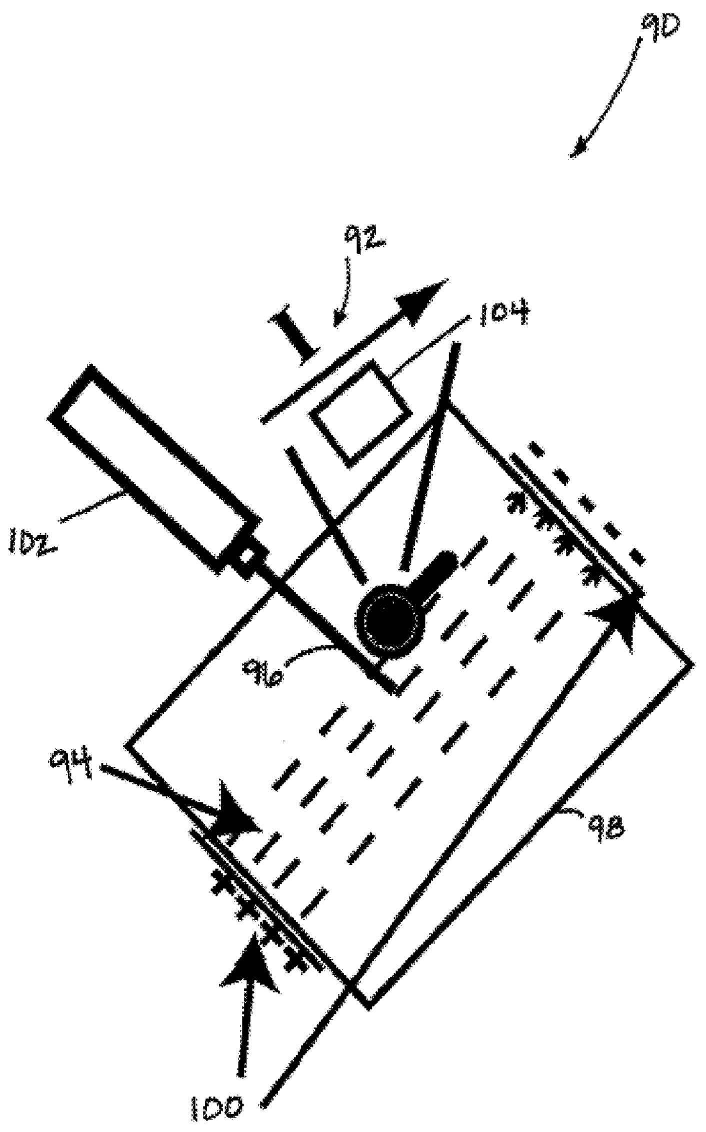
FIG. 5 is a top plan view of another exemplary embodiment of an apparatus for stimulating biological tissue implementing an optical beam for altering permittivity constructed in accordance with the principles of the present disclosure.

FIG. 5 shows a set up 90 for applying a method for generating an altered current with a newly generated displacement current 92 through the combined effects of an electric field 94 and an optical beam 96. A tissue or composite of tissues 98 is placed within electric field 94 generated by an electric source 100 and combined with optical source 102 which generates optical beam 96 that can be focused on the tissue 98. In the area that the optical beam 96 is focused on the tissue, the electric field 94 transects the sub component of tissue 104, where the optical beam 96 reacts with the tissue to alter the tissue's relative permittivity relative to the applied electric field 94, and as such generates a displacement current 92 in addition to the current that would be present due to the source electric field 94. The optical beam 96 could, for example, interact with the tissue by altering its temperature through photothermal effects and/or particle excitation, alter the distribution of ions in the cellular and extra-cellular media for instance along ionic double layers along cell walls by exciting the movement of ions optically, ionizing the tissue via laser tissue-interactions, or alter the conformation of proteins and other charged components within the tissue such that the permittivity of the tissue is altered relative to the low frequency electric field 94. In addition to the main permittivity change that occurs in the tissues, a conductivity change could also occur in the tissue, which secondarily alters the ohmic component of the currents.

In another embodiment, a thermal source to alter the permittivity of the tissue may be used. In such embodiments, a thermal source such as a heating probe, a cooling probe, or a hybrid probe may be placed external or internal to the tissue to be stimulated. A thermal source may alter the permittivity of the tissue through the direct permittivity dependence of tissue temperature, mechanical expansion of tissues in response to temperature changes, or by mechanical forces that arise due to altered particle and ionic agitation in response to the temperature alteration such that permittivity of the tissue is altered relative to an applied electric field. In addition to the main permittivity change that occurs in the tissues, a conductivity change could also occur in the tissue, which secondarily alters the ohmic component of the currents. This embodiment may be useful for stimulation in the presence of an acute injury to the tissue where the thermal source could be used to additionally assist in the treatment of the tissue injury, for example with a traumatic brain injury or an infarct in any organ such as the heart. The tissue could be cooled or heated at the same time stimulation is provided to reduce the impact of an injury.

In a further embodiment, the method according to the present disclosure is applied in the area of muscular stimulation, where amplified, focused, direction altered, and/or attenuated currents could be used to alter muscular activity via direct stimulation, depolarizing muscular cells, hyperpolarizing muscular cells, modifying membrane potentials, and/or increasing or decreasing the excitability of the muscle cells. This alteration of excitability or firing patterns can last past the duration of stimulation and thus be used as a basis to provide lasting treatment. Additionally, the stimulation can be provided in multiple, but separate sessions to have a summed, or carry-over effect, on the excitability of cells and tissue. Additionally, the stimulation could be provided to prime the tissue by adjusting the muscle cell excitability to make it more or less susceptible to alternate follow up forms of stimulation. The stimulation could be used after another form of stimulation was used to prime the tissue. Furthermore, the stimulation could be applied for a chronic period of time. This embodiment may be useful for altering or assisting cardiac pacing or function, assisted breathing, muscle stimulation for rehabilitation, muscle stimulation in the presence of nerve or spinal cord injury to prevent atrophy or assist in movement, or as substitution for physical exercise.

In yet another embodiment, the method according to the present disclosure can be applied the area of physical therapy, where amplified, focused, direction altered, and/or attenuated currents could be used to stimulate blood flow, increase or alter neuromuscular response, limit inflammation, speed the break down of scar tissue, and speed rehabilitation by applying the focus of the current generation to the effected region in need of physical therapy. It is envisioned that the method according to the present disclosure may have a wide variety in the area of physical therapy including the treatment or rehabilitation of traumatic injuries, sports injuries, surgical rehabilitation, occupational therapy, and assisted rehabilitation following neural or muscular injury. For instance, following an injury to a joint or muscle, there is often increased inflammation and scar tissue in the region and decreased neural and muscular response. Typically, ultrasound is provided to the affected region to increase blood flow to the region and increase the metabolic re-absorption of the scar tissue while electrical stimulation is provided separately to the nerves and muscles; however, by providing them together, a person could receive the benefit of each individual effect, but additionally amplified stimulatory and metabolic effects through the altered currents. The other methods for generating altered currents discussed within could also be used to assist in physical therapy via the displacement currents that are generated.

Furthermore, the method according to the present disclosure may be applied to the area of cellular metabolism, where currents could be used to interact with electrically receptive cells or charged membranes to alter the tissue or cellular dynamics. It is envisioned that this embodiment could provide treatment for various diseases where electrically receptive cells respond to the newly generated displacement currents and altered current distribution.

Furthermore, the method according to the present disclosure may be applied to the area of gene therapy. Amplified, focused, direction altered, and/or attenuated currents could be used to interact with electrically receptive cells or receptors within the cell to influence protein transcription processes and alter the genetic content of the cells. The altered current densities in the tissue can interact with the tissue to stimulate this altered gene regulation. Additionally, the displacement currents generated by the method could further be used to assist in drug delivery and/or gene therapy through the altered current influence on the delivery of agents.

Furthermore, the method according to the present disclosure may be applied to the area of tissue growth. Combined energies could be used to interact with cells or receptors within the cell to influence cell growth (and/or tissue(s)) and/or alter cellular (and/or tissue(s)) processes and/or structures. Stimulation can be used to increase and or slow cell and/or tissue growth and/or affect tumors, such as through ablation methods whereby energies can be used to ablate tissues or with methods whereby combined energies can create tumor treating fields. For instance, with electromechanical stimulation, altered electromagnetic fields generated via electromechanical coupling can affect the tissues, while in certain embodiments the mechanical fields could also have a further therapeutic effect.

The methods and devices of this disclosure involve providing a first type of energy to a region of tissue, in which the first type is provided in an amount that inhibits cellular function within the region of tissue, and providing a second type of energy to the region of tissue, in which the second type is provided in an amount that facilitates cellular function within the region of tissue, wherein the combined effect stimulates cellular function within the tissue. In certain embodiments, the stimulatory effect is facilitatory to the cellular function within the tissue (and in certain embodiments, the stimulatory effect can have a greater facilitatory effect than that of the second type of energy alone). In other embodiments, the stimulatory effect is inhibitory to the cellular function within the tissue (and in certain embodiments, the stimulatory effect can have a greater inhibitory effect than that of the first type of energy alone). For example, providing one energy type with specific parameters inhibits certain electrical, thermal, mechanical, optical, and/or chemical functions of a cell (such as in size and/or timing), yet the application of a second energy type with specific parameters facilitates certain electrical, thermal, mechanical, optical, and/or chemical functions of a cell, but the combined application of the energies leads to an inhibitory effect(s) greater than the first energy applied alone or a facilitatory effect(s) greater than the second energy type applied alone. The stimulation can be applied to affect multiple functions of the cell, whereby the combined energies could have multiple facilitatory and/or inhibitory effects on the cell (and/or the individual energies can have their own independent effects). Furthermore the methods described herein could be applied to extend (or decrease) the duration of stimulatory effect of one (or both) of the energy types on cellular function, whereby the combined effects of the two energies lead to an extended duration of effect of one (or both) of the stimulatory energies.

The direction of cellular effect (inhibitory or facilitatory) can be controlled by any of the energy types applied, depending on the energy source parameters and the targeted tissue.

For example with a transcranial DC electrical energy source applied in conjunction with a transcranial ultrasound energy source (such as might be used for imaging or stimulation), the DC electrical energy source characteristics could be used to determine the direction of typical cellular response during transcranial application (i.e., the polarity of the electrical field); for example one could apply a DC electrical field in conjunction with any typical ultrasound field transcranially to a neural target in the brain, where the DC electrical field and the ultrasound field could be provided in either a facilitatory or inhibitory manner, but the DC electric field is used determine the direction of stimulatory effect, such as could be done with a tDCS stimulation device in conjunction with an ultrasound imaging system, where the polarity of the tDCS fields are used for controlling the direction of combined effect. For instance if one provided a DC electrical field (such as what could be done transcranially from an anodal scalp electrode (with approximately 2 mA/25 cm^2 current density amplitude, as reported at the scalp source)) focused on the visual cortex while simultaneously providing an ultrasound stimulation with inhibitory properties to the same area (such as could be done with an ultrasound source providing a typical transcranial imaging signal of approximately a 2.4 MHz center frequency (where the center frequency refers to the NEMA center frequency, calculated in accordance with NEMA UD2 (NEMA Acoustic Output Measurement Standard) defined as Fc=(f1+f2)/2 where f1 and f2 are the frequencies at which the transmitted acoustic pressure spectrum is 71% (−3 dB) of its maximum value), with a Max Ispta.3 of ~0.2 W/cm^2 (the derated (at 0.3 dB/cm.MHz) Spatial-Peak Temporal-Average intensity (mW/cm^2)), the Max Isppa.3 of ~33 W/cm^2 (the derated (at 0.3 dB/cm.MHz) Spatial-Peak Pulse-Average intensity (W/$cm^2$)), and a Max Imax.3 of ~46 W/cm^2 (the derated (at 0.3 dB/cm.MHz) maximum half-cycle intensity value acquired at the depth where Pii.3 is maximized (W/cm^2))) the overall effect on the neural target would be facilitatory (although the techniques provided individually would elicit facilitatory (tDCS) and inhibitory (ultrasound) effects). However, by altering the relative position of the DC source (such as by placing it inside the brain) and both lowering its strength and reversing its polarity, such that it was a cathodal source (for further examples describing anodal vs cathodal effects see (Wagner, Valero-Cabre and Pascual-Leone, Noninvasive Human Brain Stimulation, Annu Rev Biomed Eng, 2007) or its references (Bindman, Lippold and Redfearn, The Action of Brief Polarizing Currents on the Cerebral Cortex of the Rat (1) During Current Flow and (2) in the Production of Long-Lasting after-Effects, J Physiol, 172, (369-82, 1964), (Bindman L J, Long-lasting changes in the level of the electrical activity of the cerebral cortex produced by polarizing currents, Nature 196,(584-85, 1962), (Purpura and McMurtry, Intracellular Activities and Evoked Potential Changes During Polarization of Motor Cortex, J Neurophysiol, 28,(166-85, 1965), and (Terzuolo and Bullock, Measurement of Imposed Voltage Gradient Adequate to Modulate Neuronal Firing, Proc Natl Acad Sci USA, 42,(9), 687-694, 1956)), the relative electric field effect on the visual cortex would be the same as having used the anodal stimulation on the scalp surface (and thus the combined effect would be the same, but driven by the cathodal driven electric field (but where the relative field effects are the same)). However, by flipping the polarity of the electrical source field in either example the combined effects would no longer be facilitatory, but inhibitory. (Although the general convention in transcranial brain stimulation methods is reported using the energy source positions on the scalp, one ultimately determines the direction of stimulation of the combined fields by accounting for the energy fields at the site of action (i.e., the stimulatory field(s) direction and timing at the site of the stimulated cell(s)) and thus while providing specific examples herein of transcranial applications (where we generally follow convention of reporting the effects relative from the scalp application site), the amplitude, source location, timing, and/or vector orientation of the energy fields (and direction of neural effect (i.e., inhibitory or facilitatory) can be modified by changing the location and/or characteristics of the stimulation energy source(s) (and their applied energies)).

And while above we provide an example for combined electrical and mechanical stimulation where the DC electric field is used to control the direction of effect (i.e., inhibitor/facilitatory), the relative interactions between the two energy types can be used to determine and control the stimulatory effect direction. For instance, one could also alter the ultrasound parameters instead of the electrical source characteristics to control the direction of neural effect (such as one could provide a DC electric field, but alter the direction of neural response (i.e., inhibitor/facilitatory) through the pulse shape, pulse frequency, spectral components, and/or relative direction of the mechanical fields provided by the ultrasound source (relative to the DC field)). For example, one could provide an electrical field, such as through a DC current source which was inhibitory to the neural targets (such as a cathodal application of a low intensity current to the cortex from a scalp electrode overlying the entire scalp (and thus cortex) with an indifferent electrode placed below the mouth of the individual being stimulated) but also provide a pulsed transcranial ultrasonic field to a focused target in the presence of the broad field (for example with a 0.7 MHz field, pulsed on and off (for short pulse durations, for example for a period shorter than the refractory period of the targeted cells, or for instance at a 65 microsecond duration, or just for one quarter of a wave-cycle) at a frequency greater than 20 Hz) to the same brain area. The coupling of the fields can lead to an amplified electrical current in the tissue (at the frequency in which the ultrasonic field is turned on and off), which can ultimately have a facilitatory effect on the neural targets, such as for example those in the motor cortex (one can provide the electric field at an intensity where its effects alone are negligible in the targeted region, or at a level where the combined effects are greater than that of its individual effects). As another example, one could provide the same electrical field, but alter the mechanical field such that it is pulsed on and off at a 1 Hz frequency, this in turn would lead to an overall inhibitory effect on the neural targets.

Furthermore, one could vary both of the electrical and mechanical fields (e.g., the relative timing, phase, frequency (pulse or spectral power of individual pulses), shape, dynamics, direction, and/or amplitude of the applied energy fields), such as with a control device and/or methodology whereby the field parameters are controlled and/or tuned to the desired effect (facilitatory or inhibitory (and magnitude of effect, timing of effect, duration of effect)) based on the combined field analysis relative to the neural response. These parameters could be altered continuously, whereby combined effects (that when provided individually could have contrasting effects) provide stimulatory effects that are greater than either of the individual modality applied individually.

Ultimately, one could calculate, optimize, tune, or guide the combined energy field effects (such as those driven by an electric field source and a mechanical field source) with any computational method such as those explained co-owned and co-pending U.S. patent application Ser. No. 13/216,282 the content of which is incorporated by reference herein in its entirety (and/or integrated with imaging data and/or tissue property data and/or feedback information, such as those explained co-owned and co-pending U.S. patent application Ser. No. 13/162,047 the content of which is incorporated by reference herein in its entirety).

In another potential embodiment these methods could be implemented to effectively provide 'noise' to the cellular system that is targeted, or provide continuously alternating inhibitory and facilitatory signals to alter normal cellular function (either with combined stimulatory methods (i.e., multiple energy types) and/or with individual energy types).

All of the methods and processes discussed in this document could be implemented with any form of stimulation, including but not limited to electromagnetic, mechanical, optical, thermal, electrical, magnetic, and/or combined methods (and/or methods which alter tissue impedances relative to electrical sources to generate altered stimulation currents, for example with electromagnetic, chemical, mechanical, optical, thermal, electrical, magnetic, and/or combined sources). Typically, the two energy components would be simultaneously applied; but, using one energy type to prime the tissue for one or more energy types is also possible, either sequentually applying the energies or with a period of time in between the second energy application.

Furthermore the methods demonstrated herein could be extended to work with more than just two energy types, and the direction of effect (inhibitory or facilitatory) determined via the combined energy analysis working through the different permutations as described above. As in the other methods with two energy types, the dynamics of the energy source(s) could be altered in a manner to controll direction (e.g., inhibitory, facilitroy) of the combined effect on cellular function. As in the other methods with two energy types, the direction of the neural effect with more than two energy types can be determined by the methods outlined herein in conjunction with co-pending and co-owned U.S. patent application Ser. No. 13/216,282.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

EXAMPLES

Example 1

Combination of Inhibitory and Facilitatory Amounts of Energy

Electrophysiology protocols focused on comparing the combined local visual evoked potentials (VEP) recorded from a 23 contact electrode, implanted in area 17 (i.e., primary visual cortices, V1) of anaesthetized adult cats (n=6) during and immediately following transcranial stimulations applied to the V1. Application of a mechanical field (TUS (2.4 MHz/0.2 W/$cm^2$)), an electrical field (tDCS (2 mA DC/9 $cm^2$, anodal)), a combination of a mechanical field and an electrical field (ESSstim (2 mA DC/9 $cm^2$, 2.4 MHz/0.2 W/$cm^2$)), and a SHAM (inactive transducer) were evaluated (i.e., stimulations completed transcranially from an anodal scalp electrode (with a ~2 mA/9 cm^2 current density amplitude, as reported at the scalp source) and a ultrasound scalp source (a 2.4 MHz center frequency (where the center frequency refers to the NEMA center frequency, calculated in accordance with NEMA UD2 (NEMA Acoustic Output Measurement Standard) defined as Fc=(f1+f2)/2 where f1 and f2 are the frequencies at which the transmitted acoustic pressure spectrum is 71% (−3 dB) of its maximum value), with a Max Ispta.3 of ~0.2 W/cm^2 (the derated (at 0.3 dB/cm.MHz) Spatial-Peak Temporal-Average intensity (mW/cm^2)), the Max Isppa.3 of ~33 W/cm^2 (the derated (at 0.3 dB/cm.MHz) Spatial-Peak Pulse-Average intensity (W/$cm^2$)), and a Max Imax.3 of ~46 W/cm^2 (the derated (at 0.3 dB/cm.MHz) maximum half-cycle intensity value acquired at the depth where Pii.3 is maximized (W/cm^2))). Dosing was applied for 5 min periods. Although anesthesia and low stimulation doses were used to minimize the offline/carryover effects of stimulation, each application of stimulation was followed by a variable washout period, where the real-time VEP response was monitored and allowed to return to the range of the pre-stimulation VEPs (15 min minimum, assessed in 5 min blocks).

Figure 6:
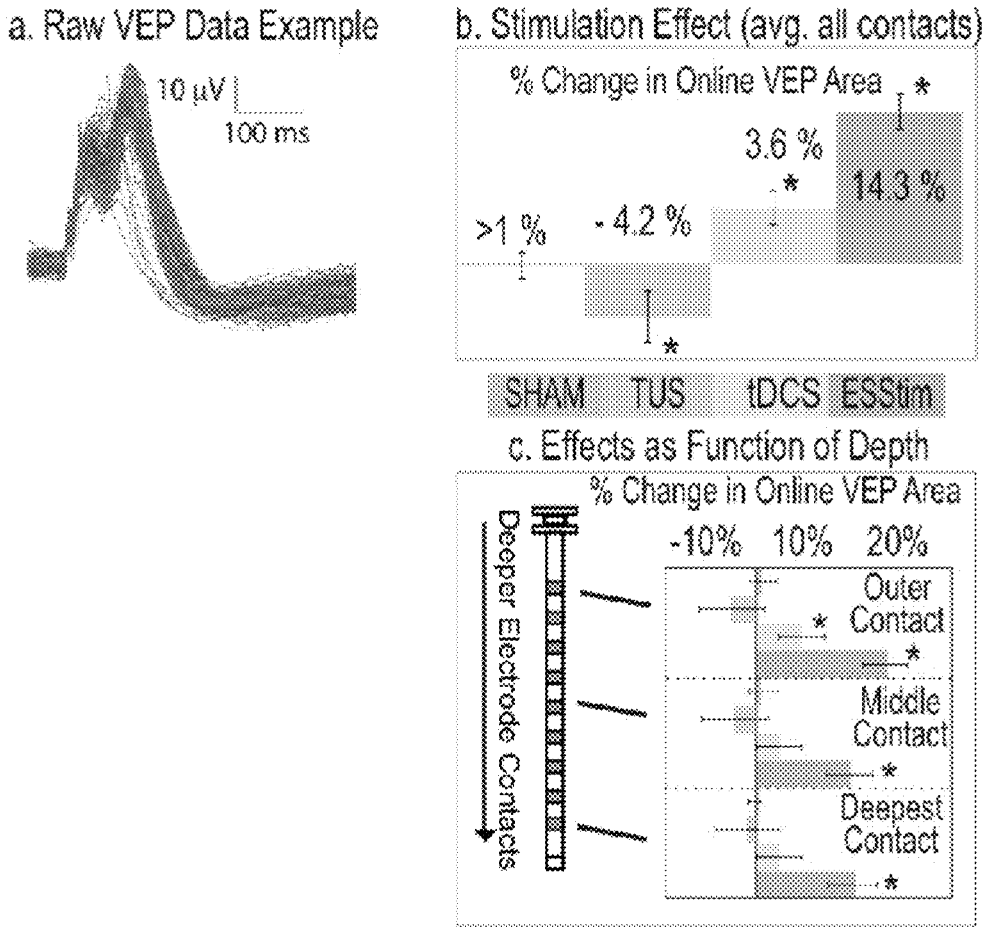
FIGS. 6A-C show a set of graphs comparing mechanical stimulation alone, electrical stimulation alone, and the combination of mechanical and electrical stimulation. Part A is a raw data example of visual evoked potentials (VEPs) shown from one animal, and one electrode contact (for readability). Part B demonstrates the stimulation effect (averaged across all contacts and animals). Part C demonstrates the depth effect of stimulation (the electrode implemented had 23 contacts (50 mm length, and 50 mm inter-contact distance), but in FIG. 3-C only 3 contacts are shown for readability). Throughout the figure, * indicates significance, which was determined first by an N-way Anova, as explained in the examples section, with a subsequent multiple comparison of means (with LSD correction).

A 3-way ANOVA (Dependent: Area Under VEP Curve (i.e., measure of cortical excitability); Independent: Stimulation Type, Time, and Cat) demonstrated a highly significant effect of stimulation type ($F_{3,14699}$=73.97, p≈0), time (analyzed in 5 minute epochs (i.e., online, 0-5, 5-10, and 10-15 mins)) ($F_{3,14699}$=90.68, p≈0), and cat ($F_{5,14699}$=40.31, p≈0). A subsequent comparison of the means (with a least squares difference (LSD) correction, with p set as p<0.05), demonstrated a significant difference between all of the techniques during their online periods. It was observed that application of the mechanical field alone had a suppressive effect on cellular function within the region of tissue, and that application of the electric field had a facilitatory effect on cellular function within the region of tissue. See FIG. 6A-C. It was observed that combining the mechanical field and the electrical field at the same dosing as they were applied individually facilitated cellular function within the tissue, and that the stimulation of cellular function was approximately 4 times greater than the stimulation of cellular function observed from the electrical field alone. See FIG. 6A-C.

A secondary analysis of the techniques as a function of stimulation type, time, and contact depth ($F_{367,14388}$=3.24, p≈0) accounting for cat to cat variability was undertaken where a multiple comparison of means, with an LSD correction(p<0.05), demonstrated the online effects of the combination of the mechanical field and the electrical field to be significant throughout every contact (from surface to deeper contacts) and the electrical field to only be significant at the cortical surface. The mechanical field alone had an insignificant effect at any individual contact site but was consistently suppressive (See FIG. 6A-C).

Finally, in a sub cat group (n=3 complete), randomized transcranial stimulations to the V1, the frontal eye field (A6), and the posterior middle suprasylvian sulcus (PMS) areas have been made with comparisons being made among a combination of a mechanical field and electrical field, an electrical field alone, a mechanical field alone, and a SHAM field (i.e., inactive transducers). In these animals, the results demonstrated V1 and PMS stimulation effects similar to above (with the V1 stimulations demonstrating a slightly larger effect than PMS, although not greatly different); and in the deepest target (A6), the combination of the mechanical field and the electrical field was the only technique to demonstrate any consistent effect in neural activity (approximately +5.8% change in the VEP magnitude).

What is claimed is:

1. A method for stimulating cellular function within tissue, the method comprising:

providing an electrical type of energy to a location in a region of tissue; and providing a non-electrical type of energy to the location in the region of tissue;

wherein one type is provided in an amount that inhibits cellular function within the location in the region of tissue, the other type is provided in an amount that facilitates cellular function within the location in the region of tissue, and the combined effect stimulates cellular function within the tissue in a manner in which the stimulatory effect exceeds the combined effect of the two amounts of energy provided to the region of tissue.

2. The method according to claim 1, wherein the stimulatory effect is facilitatory to the cellular function within the tissue.

3. The method according to claim 1, wherein the stimulatory effect is inhibitory to the cellular function within the tissue.

4. The method according to claim 1, wherein the electrical and non-electrical types are provided simultaneously.

5. The method according to claim 1, wherein the electrical and non-electrical types are provided sequentially.

6. The method according to claim 1, wherein the non-electrical type of energy is a mechanical type of energy.

7. The method according to claim 6, wherein the mechanical type of energy is generated by an ultrasound device.

8. The method according to claim 7, wherein the mechanical type of energy is pulsed.

9. The method according to claim 7, wherein the mechanical type of energy is time varying.

10. The method according to claim 7, wherein the mechanical type of energy is pulsed a plurality of time, and each pulse may be for a different length of time.

11. The method according to claim 1, wherein the electric type of energy is pulsed.

12. The method according to claim 1, wherein the electric type of energy is time varying.

13. The method according to claim 1, wherein the electric type of energy is pulsed a plurality of time, and each pulse may be for a different length of time.

14. The method according to claim 1, wherein the electric type of energy is time invariant.

15. The method according to claim 1, wherein the electrical and non-electrical types of energy are applied to a structure or multiple structures within the brain or the nervous system selected from the group consisting of: dorsal lateral prefrontal cortex, any component of the basal ganglia, nucleus accumbens, gastric nuclei, brainstem, thalamus, inferior colliculus, superior colliculus, periaqueductal gray, primary motor cortex, supplementary motor cortex, occipital lobe, Brodmann areas 1-48, primary sensory cortex, primary visual cortex, primary auditory cortex, amygdala, hippocampus, cochlea, cranial nerves, cerebellum, frontal lobe, occipital lobe, temporal lobe, parietal lobe, sub-cortical structures, and spinal cord.

16. The method according to claim 1, wherein the tissue is neural tissue.

17. The method according to claim 16, wherein the effect of the stimulation alters neural function past the duration of stimulation.

* * * * *